(12) United States Patent
Muni et al.

(10) Patent No.: US 6,375,629 B1
(45) Date of Patent: Apr. 23, 2002

(54) CORE WIRE WITH SHAPEABLE TIP

(75) Inventors: Ketan P. Muni; Sivette Lam, both of San Jose; Juan T. Domingo, Union City; Gholam-Reza Zadno-Azizi, Newark; Samuel Omaleki, Morgan Hill; Isaac J. Kim, San Jose; Celso J. Bagaoisan, Union City, all of CA (US)

(73) Assignee: Medtronic PercuSurge, Inc., Sunnyvale, CA (US)

( * ) Notice: Subject to any disclaimer, the term of this patent is extended or adjusted under 35 U.S.C. 154(b) by 0 days.

(21) Appl. No.: 09/690,588

(22) Filed: Oct. 17, 2000

Related U.S. Application Data

(62) Division of application No. 09/026,357, filed on Feb. 19, 1998, now Pat. No. 6,190,332.

(51) Int. Cl.⁷ .................................................. A61B 5/00
(52) U.S. Cl. ........................................ 600/585; 72/135
(58) Field of Search ............................... 600/434, 435, 600/585; 604/280–283; 72/135

(56) References Cited

U.S. PATENT DOCUMENTS

| 3,144,868 A | 8/1964 | Jascalevich |
| 4,445,892 A | 5/1984 | Hessein et al. |
| 4,468,216 A | 8/1984 | Muto |
| 4,511,354 A | 4/1985 | Sterling |
| 4,573,470 A | 3/1986 | Samson et al. |
| 4,573,966 A | 3/1986 | Weikl et al. |
| 4,616,652 A | 10/1986 | Simpson |
| 4,616,653 A | 10/1986 | Samson et al. |
| 4,665,906 A | 5/1987 | Jervis |
| 4,723,936 A | 2/1988 | Buchbinder et al. |
| 4,748,982 A | 6/1988 | Horzewski et al. |
| 4,763,654 A | 8/1988 | Jang |
| 4,771,778 A | 9/1988 | Mar |
| 4,793,350 A | 12/1988 | Mar et al. |
| 4,838,268 A | 6/1989 | Keith et al. |
| 4,846,174 A | 7/1989 | Willard et al. |

(List continued on next page.)

FOREIGN PATENT DOCUMENTS

| EP | 0 442 480 A1 | 8/1991 |
| EP | 0 631 792 A1 | 1/1995 |
| EP | 0 661 073 A1 | 7/1995 |
| EP | 0 770 404 A1 | 5/1997 |
| EP | 0 784 991 A2 | 7/1997 |
| EP | 0 812 828 A1 | 12/1997 |
| EP | 0 823 261 A2 | 2/1998 |
| EP | 0 868 924 A2 | 10/1998 |
| WO | WO 92/00775 | 1/1992 |
| WO | WO 96/07351 | 3/1996 |
| WO | WO 96/13295 | 5/1996 |
| WO | WO 96/15824 | 5/1996 |
| WO | 97/11735 | 4/1997 |
| WO | WO 97/44084 | 11/1997 |

*Primary Examiner*—Max Hindenburg
(74) *Attorney, Agent, or Firm*—Knobbe, Martens, Olson & Bear, LLP

(57) ABSTRACT

The present invention provides an improved core wire for use in a medical catheter. In one aspect, the invention provides a core wire with a shapeable tip and method of manufacturing the same. A core wire previously made superelastic is subject to additional processing to remove its superelasticity thereby allowing the material to be shapeable to aid in advancing the core wire through a blood vessel or other body cavities. In another aspect of the present invention, a method is provided for securing the core wire to the distal end of an elongated catheter tubular body. The tubular body is mechanically crimped onto the core wire to secure the core wire in place. This crimping method has been found to increase the strength of the bond between the core wire and the catheter tube so that greater pull force is required to break the core wire off from the catheter.

17 Claims, 6 Drawing Sheets

U.S. PATENT DOCUMENTS

| | | |
|---|---|---|
| 4,846,193 A | 7/1989 | Tremulis et al. |
| 4,917,088 A | 4/1990 | Crittenden |
| 4,943,278 A | 7/1990 | Euteneuer et al. |
| 4,946,466 A | 8/1990 | Pinchuk et al. |
| 4,964,409 A | 10/1990 | Tremulis |
| 4,976,720 A | 12/1990 | Machold et al. |
| 4,998,917 A | 3/1991 | Gaiser et al. |
| 5,042,985 A | 8/1991 | Elliott et al. |
| 5,059,178 A | 10/1991 | Ya |
| 5,159,937 A | 11/1992 | Tremulis |
| 5,163,906 A | 11/1992 | Ahmadi |
| 5,167,239 A | 12/1992 | Cohen et al. |
| 5,211,636 A | 5/1993 | Mische |
| RE34,466 E | 12/1993 | Taylor et al. |
| 5,312,340 A | 5/1994 | Keith |
| 5,322,508 A | 6/1994 | Viera |
| 5,341,818 A | 8/1994 | Abrams et al. |
| 5,368,049 A | 11/1994 | Ramen et al. |
| 5,387,225 A | 2/1995 | Euteneuer et al. |
| 5,411,476 A | 5/1995 | Abrams et al. |
| 5,417,658 A | 5/1995 | Loney et al. |
| 5,423,742 A | 6/1995 | Theron |
| 5,439,000 A | 8/1995 | Gunerson et al. |
| 5,449,343 A | 9/1995 | Samson et al. |
| 5,451,209 A | 9/1995 | Ainsworth et al. |
| 5,462,529 A | 10/1995 | Simpson et al. |
| 5,486,183 A | 1/1996 | Middleman et al. |
| 5,500,180 A | 3/1996 | Anderson et al. |
| 5,558,643 A | 9/1996 | Samson et al. |
| 5,567,203 A | 10/1996 | Euteneuer et al. |
| 5,601,572 A | 2/1997 | Middleman et al. |
| 5,637,089 A | 6/1997 | Abrams et al. |
| 5,640,970 A | 6/1997 | Arenas |
| 5,706,826 A | 1/1998 | Schwager |
| 5,782,741 A | 7/1998 | Bradshaw et al. |

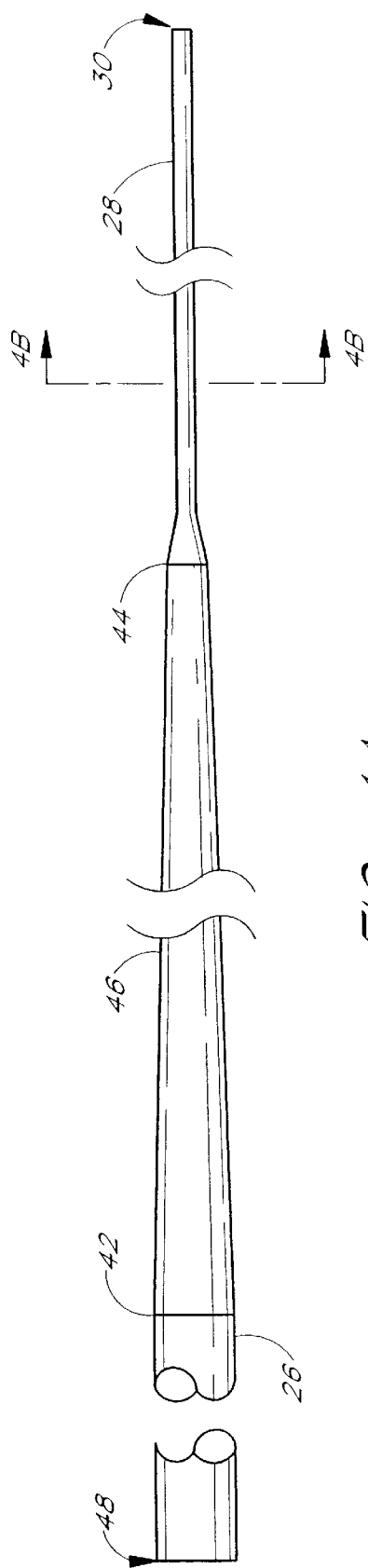
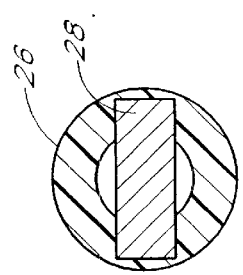
FIG. 4A
FIG. 4B

CORE WIRE WITH SHAPEABLE TIP

This application is a divisional of U.S. patent application Ser. No. 09/026,357, filed Feb. 19, 1998 now U.S. Pat. No. 6,190,332.

BACKGROUND OF THE INVENTION

1. Field of the Invention

The present invention relates generally to surgical device design and fabrication and, more particularly, to core wires for use in catheters and the like.

2. Description of the Related Art

Medical catheters, such as guidewires and balloon catheters, have been proven efficacious in treating a wide variety of blood vessel disorders. Moreover, these types of catheters have permitted clinicians to treat disorders with minimally invasive procedures that, in the past, would have required complex and perhaps life threatening surgeries. For example, balloon angioplasty is now a common procedure to alleviate stenotic lesions (i.e., clogged arteries) in blood vessels, thereby reducing the need for heart bypass operations.

Because medical catheters must be passed through a tortuous blood vessel network to reach the intended treatment site, it is desirable that the catheters be fairly flexible, especially at the distal end. However, the distal end must not be so flexible that it tends to bend back upon itself when the clinician advances the catheter distal end through the patient.

One method of imparting desired flexibility characteristics to a catheter has been to incorporate a "core wire" into the distal end of the catheter. A core wire is a wire that extends from the distal end of a catheter body, providing structural support to the distal end to prevent bend backs or kinks during catheter advancement. Furthermore, the core wire is also flexible, such that the catheter distal end may navigate tortuous blood vessel networks or other body cavities.

Previously known catheter core wires may not be sufficiently rigid at the very distal tip of the wire. In particular, catheter core wires are commonly formed of superelastic materials such as NiTi alloys which exhibit an elastic response when subject to stress. Superelasticity refers to the ability of a material to undergo deformation and to return to its original configuration without being permanently or "plastically" deformed. This superelasticity, often referred to as transformational superelasticity, exhibits itself as the parent crystal structure of the material as it transforms into a different crystal structure. In superelastic materials the parent crystal structure is known as the austenitic phase and the product crystal structure is known as the martensitic phase. Such formed martensite is termed stress-induced martensite.

While superelasticity may be desirable for the majority of the core wire, superelasticity at the very distal tip of the core wire creates the problem that the tip will not be shapeable. Shapeability is desirable so that a doctor or other person inserting the catheter into the body can shape the tip into a form advantageous for insertion and navigation through the body. If the tip of the core wire is superelastic, the material cannot be shaped.

An additional problem with previously known core wires is that they may not be securely attached to the distal end of the catheter. What is needed is a method to make the connection between the catheter and the core wire secure so that these stress of vascular navigation will not cause breakages.

SUMMARY OF THE INVENTION

The present invention addresses the needs raised above by providing an improved core wire for use in a medical catheter. In one aspect of the invention, there is provided a core wire with a shapeable tip and method of manufacturing the same. A core wire previously made superelastic is subject to additional processing to remove superelasticity from a distal tip, thereby allowing the material at the distal tip to be shapeable to aid in advancing the core wire through a blood vessel or other body cavities.

In one embodiment, the core wire is manufactured by first providing an elongate body of NiTi alloy or similar material. This elongate body is subject to a first cold working in the range of about 20 to 40%. A heat treatment in the range of about 300° to 600° C. for 10 seconds to 60 minutes is performed to impart superelasticity to the body. Following heat treatment, the distal end of the core wire is cold worked from about 10 to 50%, removing superelasticity from this end and producing a shapeable tip at the end of the core wire. The core wire that results is a flexible, superelastic body having a shapeable distal tip with no superelasticity.

Alternatively, once the NiTi is imparted with superelasticity, the distal end of the core wire can be removed of its superelasticity by an additional heat treatment. Heat treatments at temperatures of about 400–800° C. for extended periods of time will cause the material to lose its superelasticity at the distal end. Additionally, superelasticity can be imparted to the core wire by a solution treatment followed by aging process.

In another embodiment of the present invention, a method is provided for securing the core wire to the distal end of an elongated catheter tubular body. Conventional means for attaching a core wire to a catheter body is by soldering, which uses flux of hydrogen. NiTi alloys are susceptible to hydrogen embrittlement, which will in turn diminish the tensile strength of the material. Because of the stresses involved in advancing the catheter through a vessel network, it has been discovered that a core wire soldered to a catheter may break off during catheter advancement. In one aspect of the present method, the tubular body is mechanically crimped onto the core wire to secure the core wire in place. This crimping method has been found to increase the strength of the bond between the core wire and the catheter tube so that greater pull force is required to break the core wire off from the catheter.

BRIEF DESCRIPTION OF THE DRAWINGS

FIG. 4A is a side view of the core wire manufactured in accordance with the preferred method of the present invention.

FIG. 4B is a cross-sectional view along line 4B—4B of the core wire of FIG. 4A.

DETAILED DESCRIPTION OF THE PREFERRED EMBODIMENTS

Figure 1:
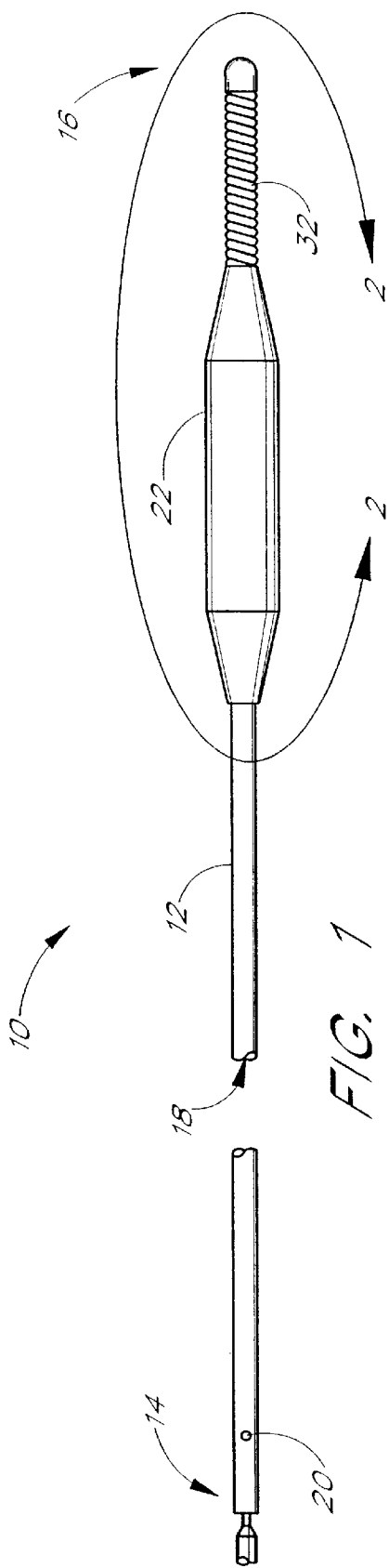
FIG. 1 is a side view of a catheter incorporating the core wire of one embodiment of the present invention.

Referring to FIG. 1, there is depicted a catheter 10 incorporating the core wire in accordance with the preferred embodiment of the present invention. Although the core wire is depicted and discussed in the context of being part of a simple occlusive device having a single lumen, it should be appreciated that the principles and aspects of the present invention are applicable to more complex occlusive devices having structures and functionalities not discussed herein. For example, the present inventors contemplate that the core wire of the present invention may be used in occlusive devices functioning as anchorable guide wires or filters. In addition, the core wire of the present invention is also applicable to catheters having other types of balloons, such as latex or silicone, or to catheters used for dilatation balloons, made of materials such as polyethylene terephthalate. Moreover, the core wire of the present invention may also be adapted to other types of non-balloon catheters, such as irrigation catheters used in drug delivery or radiation therapy. The tip design of the core wire can also be applicable to ordinary guidewires. In this case the guidewire may be hollow or solid. The manner of adapting the core wire of the present invention to these various structures and functionalities will become readily apparent to those of skill in the art in view of the description which follows.

Guidewires and Catheters

Figure 2:
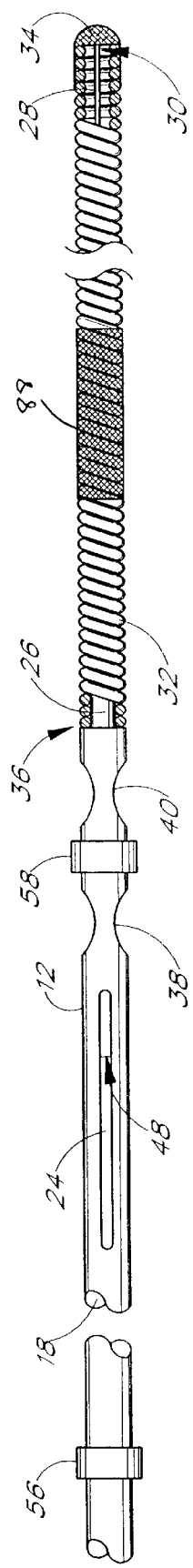
FIG. 2 is a longitudinal partial sectional view of a distal portion of the catheter implementing the preferred core wire before balloon mounting.

FIGS. 1 and 2 illustrate a guidewire or similar catheter incorporating a preferred embodiment of the core wire of the present invention. The manufacture and construction of the core wire is described in more detail below in connection with FIGS. 3 and 4, respectively. Referring to FIG. 1, catheter 10 generally comprises an elongate flexible tubular body 12 extending between a proximal control end 14, corresponding to a proximal section of the tubular body 12, and a distal functional end 16, corresponding to a distal section of tubular body 12. Tubular body 12 has a central lumen 18 which extends between ends 14 and 16. An inflation port 20 is provided on tubular body 12 near the proximal end 14. Inflation port 20 is in fluid communication with lumen 18, such that fluid passing through inflation port 20 into or out of lumen 18 may be used to inflate or deflate inflatable balloons in communication with lumen 18. Lumen 18 is sealed fluid tight at distal end 16. Inflation port 20 may be similar to existing female luer lock adapters or would be a removable valve at the end, as disclosed in assignee's co-pending application entitled LOW PROFILE CATHETER VALVE AND INFLATION ADAPTER, application Ser. No. 08/975,723, filed Nov. 20, 1997, now U.S. Pat. No. 6,050,972, the entirety of which is incorporated by reference.

The length of tubular body 12 may be varied considerably depending upon the desired application. For example, where catheter 10 serves as a guidewire for other catheters in a conventional percutaneous transluminal coronary angioplasty procedure involving femoral artery access, tubular body 12 is comprised of a hollow hypotube having a length in the range of from about 160 to about 320 centimeters with a length of about 180 centimeters being optimal for a single operator device and 300 centimeters for over the wire applications. Alternately, for a different treatment procedure, not requiring as long a length of tubular body 12, shorter lengths of tubular body 12 may be provided. Moreover, the catheter 10 may comprise a solid body rather than a hollow hypotube.

Tubular body 12 generally has a circular cross-sectional configuration with an outer diameter within the range of from about 0.008 inches to 0.14 inches. In many applications where catheter 10 is to be used as a guidewire for other catheters, the outer diameter of tubular body 12 ranges from 0.010 inches to 0.038 inches, and preferably is 0.014 to 0.018 inches in outer diameter or smaller. Non-circular cross-sectional configurations of lumen 18 can also be adapted for use with the present invention. For example, triangular, rectangular, oval, and other non-circular cross-sectional configurations are also easily incorporated for use with the present invention, as will be appreciated by those of skill in the art.

Tubular body 12 has sufficient structural integrity, or "pushability," to permit catheter 10 to be advanced through vasculature to distal arterial locations without buckling or undesirable kinking of tubular body 12. It is also desirable for tubular body 12 to have the ability to transmit torque, such as in those embodiments where it may be desirable to rotate tubular body 12 after insertion into a patient. A variety of biocompatible materials, known by those of skill in the art to possess these properties and to be suitable for catheter manufacture, may be used to produce tubular body 12. For example, tubular body 12 may be made of a stainless steel material such as Elgiloy™, or may be made of polymeric materials such as nylon, polyimide, polyamides, polyethylene or combinations thereof. In one preferred embodiment, the desired properties of structural integrity and torque transmission are achieved by forming tubular body 12 out of an alloy of titanium and nickel, commonly referred to as nitinol. In a more preferred embodiment, the nitinol alloy used to form tubular body 12 is comprised of about 50.8% nickel and the balance titanium, which is sold under the trade name Tinel™ by Memry Corporation. It has been found that a catheter tubular body having this composition of nickel and titanium exhibits an improved combination of flexibility and kink resistance in comparison to other materials. Further details are disclosed in assignee's co-pending applications entitled HOLLOW MEDICAL WIRES AND METHODS OF CONSTRUCTING SAME, application Ser. No. 08/812,876, filed Mar. 6, 1997, now U.S. Pat. No. 6,068,623, and SHAFT FOR MEDICAL CATHETERS, application Ser. No. 09/026,105, filed Feb. 19, 1998, now U.S. Pat. No. 6,288,072, both of which are hereby incorporated by reference.

As illustrated in FIG. 1, an expandable member such as an inflatable balloon 22 is mounted on tubular body 12. Balloon 22 may be secured to tubular body 12 by any means known to those skilled in the art, such as adhesives or heat bonding. In one preferred embodiment, balloon 22 is a compliant balloon formed out of a material comprising a block polymer of styrene-ethylene-butylene-styrene, as disclosed in assignee's co-pending application entitled BALLOON CATHETER AND METHOD OF MANUFACTURE, application Ser. No. 09/026,225, filed Feb. 19, 1998 of which is incorporated by reference.

Referring to FIG. 2, a distal portion of tubular body 12 is shown before mounting of the balloon 22. A notch 24 is provided in the tubular body 12 to allow fluid communication between the inner lumen 18 and the balloon 22 (not shown) attached to the tubular body 12. An elongate body or core wire 26 is provided at the distal end 36 of the tubular body 12, and extends within the inner lumen 18 of the tubular body 12 to a position visible through the notch 24. Adhesive stops 56, 58 are provided on tubular body 12 to prevent adhesive bonding of the balloon 22 past the location of the stops, as disclosed in the above-referenced application BALLOON CATHETER AND METHOD OF MANUFACTURE, application Ser. No. 09/026,225, filed Feb. 19, 1998.

Core wire 26 is preferably formed of a shape memory alloy, such as nitinol, but may also be formed of other materials, such as stainless steel. The core wire 26 extends from a proximal end 48, corresponding to a proximal section of the core wire, to a distal end 30, corresponding to a distal section of the core wire. The core wire 26 has a flattened tip 28 at its distal end 30, as described in more detail below in connection with FIGS. 3 and 4. Core wire 26 may range in length from about 20 mm to 100 mm, or more preferably from about 25 mm to 50 mm, and for most occlusive device applications, is typically about 40 mm. In one preferred embodiment, the length of the core wire is about 37 mm. Flattened tip 28 extends from the distal end 30 for a length between about 5 and 10 mm, and more preferably about 7.5 mm.

As shown in FIG. 2, coil 32 is provided around the core wire 26 and extends substantially along the entire length of core wire 26, from the distal end 30 of core wire 26 to the distal end 36 of tubular body 12. Coil 32 is soldered at the distal tip 30 of the core wire 26 forming a ball 34. Coil 32 is secured to the distal end 36 of tubular body 12 by suitable means such as soldering, brazing, or by an adhesive, as described in more detail below. One preferred adhesive type for connecting coil 32 to tubular body 12 is a cyanoacrylate such as LOCTITE 4011, although, as will be appreciated by those of skill in the art, other similar adhesives adopted to form metal to metal bonds may also be used. Coil 32 is formed of a suitable radiopaque material such as gold, platinum or a platinum alloy. Coil 32 can have a suitable outside diameter which corresponds to the outer diameter of tubular body 12, and can have a suitable length ranging from about 10 to about 50 mm. For example, where tubular body 12 has an outer diameter of 0.014 inches, and core wire 26 has a length of 37 mm, coil 32 may have a length of about 35 mm.

As described in more detail below, the core wire 26 and the coil 32 are formed into a subassembly prior to attachment to tubular body 12. Once the coil 32 is attached to the core wire, the proximal end 48 of core wire 26 is inserted into tubular body 12 at distal end 36. Two crimps 38 and 40 are provided near the distal end 36 of the tubular body 12 to secure the core wire 26 to the tubular body. The crimps are preferably located in a location between the notch 24 and the distal tip 36 of the tubular body 12. The crimps are preferably located a distance 0.5 to 1.5 mm apart, and more preferably, about 1.0 mm apart. The more distal crimp 40 preferably is located about 0.5 mm from the distal tip 36 of tubular body 12.

Manufacture of the Core Wire

Figure 3A:
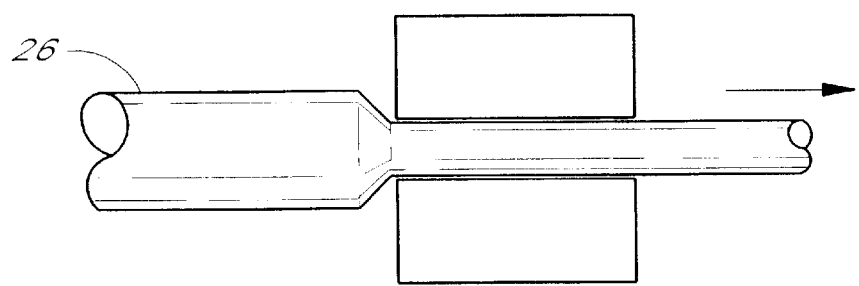
FIG. 3A is a schematic view of a first process step for producing the core wire.

Referring to FIGS. 3A, 3B, 3C and 3D, the core wire 26 can be manufactured by facilitating various thermal and/or mechanical treatments. The alloy comprising the core wire is preferably a NiTi or other superelastic alloy with a length preferably from about 20 to 50 mm, and more preferably with a length of about 37 mm. The alloy can be made superelastic by cold working the material and then heat treating the alloy. In the first step, a cold work can be performed to reduce the core wire diameter. Various facilitating instruments such as swager, metal extrusion and drawing equipment can be utilized to provide cold work. In a preferred embodiment, the core wire 26 is shaped by wire drawing the material at a preferred cold work range of about 20–40%, as shown in FIG. 3A.

Figure 3B:
FIG. 3B is a schematic view of a second process step for producing the core wire.

In step two of the process shown in FIG. 3B, following the cold work the core wire is preferably heat treated at a temperature range between about 300 and 600° C. This heat treatment can preferably be done in a salt bath, such as potassium nitrate, or in a protective atmosphere, such as Argon gas, for about 10 seconds to 60 minutes. In this embodiment, the heat treated core wire 26 may not be quenched but preferably cooled down to room temperature in a protective atmosphere. This heat treatment imparts superelastic characteristics to the core wire. Heat treatments below 750° C. do not result in heavy oxidation and therefore may be performed in air.

Figure 3C:
FIG. 3C is a schematic view of a third process step for producing the core wire.

Step three in the process shown in FIG. 3C provides the core wire 26 with a tapered configuration toward its distal end. The tapering of the wire may be produced by a centerless grinding technique or similar method as would be known to one skilled in the art. In one preferred embodiment, for a core wire with a length of about 37 mm, the wire 26 may be tapered over a distance of about 30 mm.

Figure 3D:
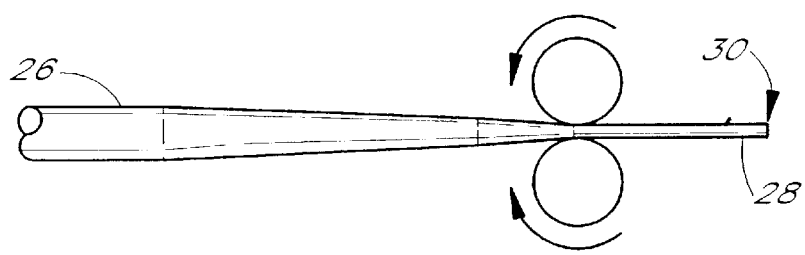
FIG. 3D is a schematic view of a fourth process step for producing the core wire.

The fourth step of the process shown in FIG. 3D is to remove the superelasticity from the distal end of the core wire by providing an additional cold work at the distal end 30. This cold work is preferably performed by rollers to produce a flattened tip 28 at a length about 5–10 mm from the distal end 30, and more preferably for a length of about 7.5 mm. The preferred cold work range is between about 10 and 50%, and more preferably about 40%. Alternate means for cold working the distal end of the core wire may be used, such as wire drawing or neutron radiation, or other means that would be known to those skilled in the art. As a result of the cold working, the nitinol core wire deforms to a cold worked martensite phase.

As shown in FIG. 4A, the core wire that results from the above described manufacturing has a constant cross-section from proximal end 48 to a boundary 42, and then tapers in an extending portion 46 from a greater diameter at boundary 42 to a smaller diameter at second boundary 44 towards the distal end 30 of the wire 26. The cross-sectional area of extending portion 46 decreases by at least about 20%, preferably by at least about 60%, more preferably by about 70%, and optimally by about 80% or more. In one embodiment, the core wire has a diameter of about 0.075 inches at boundary 42 and a diameter of about 0.003 inches at boundary 44. Beyond boundary 44, a region of constant cross-section 28 is provided where the core wire has a planar configuration, as shown in FIG. 4B. This flattened, constant cross-sectional area preferably has a length of between about 5 and 10 mm, and more preferably a length of about 7.5 mm. The thickness of the tip is preferably in the range of about 0.001 to 0.004 inches, and more preferably, about 0.002 inches.

As shown in FIG. 4A, the core wire 26 has a proximal section extending from proximal end 48 to the boundary 44 between the tapered section 46 and the flattened tip region 28 which is superelastic. The core wire 26 has a distal section with a flattened tip portion 28 exhibiting no superelasticity. Elastic characteristics of the nitinol alloys can be best viewed by the stress strain diagrams obtained from various mechanical testing methods such as tensile tests, torsion tests, bending tests or compression tests. Among these methods, the tensile test emerges as the most common mechanical testing method. In particular, tensile tests provide very useful information about both the type of deformation and the amount of deformation that a test sample undergoes under an applies stress. In this respect, FIG. 5, which shows the stress-strain relationship of the proximal and distal sections of core wire 26, provides very valuable information about the deformation characteristics of the nitinol alloy under tensile test conditions.

Figure 5:
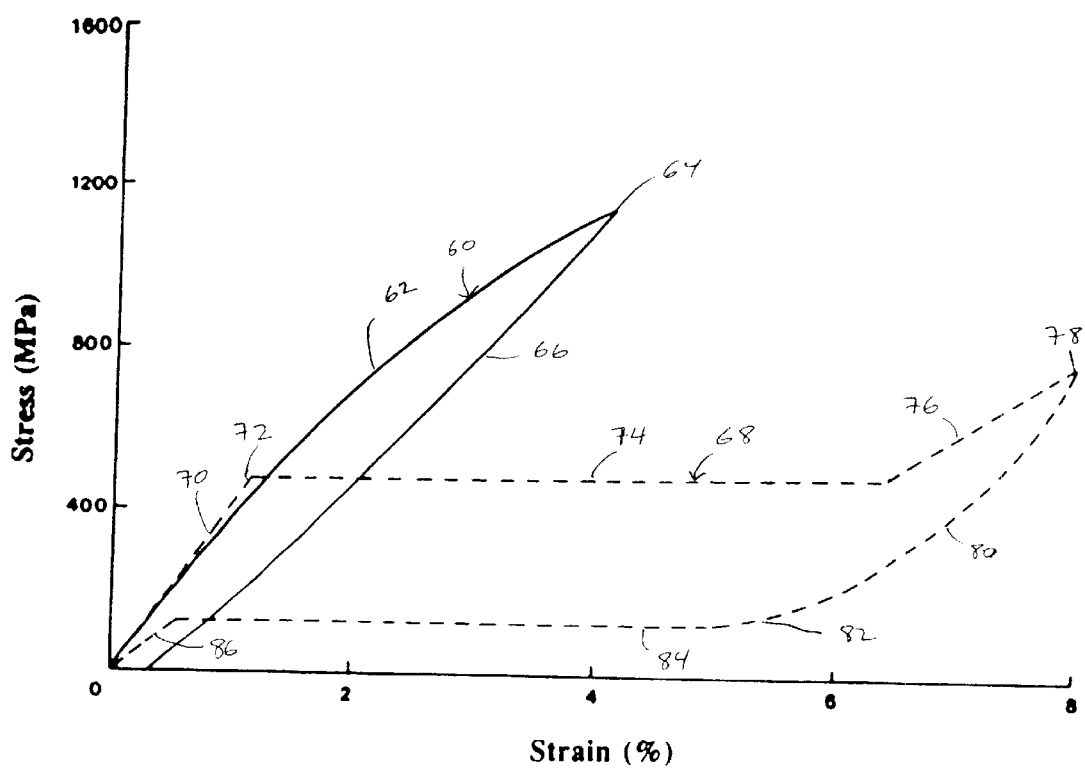
FIG. 5 is a graph comparing the elastic characteristics at the proximal end and at the distal tip of the core wire.

As shown in FIG. 5, the core wire 26 in general exhibits two different types of elastic deformation characteristics. The first deformation characteristics is shown by the solid curve 60, corresponding to the stress-strain behavior of the distal tip 28. Under the applied stress the curve 60 follows a substantially linear path 62, wherein the material elastically deforms up to a point 64, and upon unloading follows a substantially linear unloading curve 66. There is a slight non-linearity in loading and unloading which causes a hysteresis in strain. The material at the tip 28 can thus be deformed to about 4% with less than about 0.3% permanent set.

FIG. 5 also shows a stress-strain curve 68 of the proximal section of the core wire 26. Under the applied stress the curve 68 follows a substantially linear path 70 where the austenitic phase elastically deforms. The austenitic phase elastically deforms with increasing stress up to a critical yielding stress value 72 where martensitic transformation begins. After this critical stress point 72, the material continues to transform into martensite. Throughout the transformation, despite a constant increase in deformation rate of the material, the applied stress remains about the same critical stress value 72 thereby revealing the superelastic property of the material. This superelastic behavior forms a loading plateau 74 on the curve 68 until the entire austenite phase transforms into the martensite phase.

Still referring to FIG. 5, at the end of transformation, the curve 68 no longer follows a straight path but a linearly increasing path 76 where the martensitic material elastically deforms up to a point 78 where unloading begins. During the unloading, the martensite structure transforms into austenite structure. Due to internal friction, there is not an overlap of loading and unloading, and the unloading curve moves down to lower stress values. During the course of unloading, the martensitic phase is first unloaded along the substantially linear portion 80 of curve 68. At a critical stress value 82, martensite to austenite transformation begins and continues along the unloading plateau 84. Upon completion of austenitic transformation, the elastic deformation on austenitic material is unloaded along the linear portion 86.

Thus, the core wire that results is substantially flexible in a proximal section and has less flexibility, and thus, greater shapeability, at a distal tip. In one preferred embodiment, the flexibility in the proximal section results from the material being processed to exhibit transformational superelasticity, i.e., having an austenite phase which will transform to a martensite phase upon the application of stress. The shapeability of the distal section results from the fact that the distal tip 28, because of processing as described above, is in a martensitic phase, and thus exhibits only substantially linear elasticity.

Other processing than the steps described above may be used to impart flexibility and shapeability to the different portions of core wire 26. For instance, instead of cold working and heat treating the wire as shown in FIGS. 3A and 3B, the core wire can be made superelastic by a solution treatment followed by aging process. Solution treatment temperatures are preferably above about 500° C., more preferably above about 700° C., and in one preferred embodiment, about 750° C. Following solution treatment, the core wire is quenched followed by aging. Aging temperatures are preferably in the range of about 300° to 500° C., and more preferably about 350° C.

In addition, superelasticity can be removed from the distal end of core wire 26 by providing an additional heat treatment on the distal end. The heat treatment can be performed with or without need for the second cold work step described in FIG. 3D. The heat treatment preferably occurs at a temperature between about 400° and 800° C. For a temperature of 400° C., a heat treatment for about an hour or more is necessary to remove superelasticity from the core wire. For a temperature of 800° C., a heat treatment for about ten minutes or more will remove superelasticity. Other combinations of temperature and time of heat treatment to remove superelasticity from the wire as would be known to those skilled in the art. The resulting material at the distal end is in a martensite phase having substantially linear elasticity.

Securing the Core Wire to the Tubular Body

Figure 6:
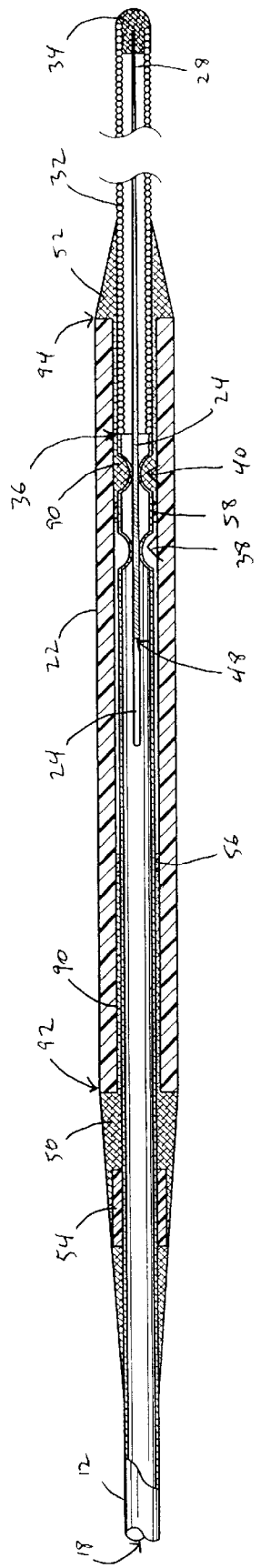
FIG. 6 is a longitudinal cross-sectional view of a distal portion of the catheter implementing the preferred core wire after balloon mounting.

Referring again to FIG. 2, and also to FIG. 6 showing a cross-section of the assembled distal end of catheter 10, there is depicted tubular body 12 incorporating a core wire manufactured by the present invention. The catheter 10 shown in FIG. 6, in addition to showing the tubular body 12, core wire 26 and coil 32 as shown in FIG. 2, also depicts the balloon 22 mounted on the tubular body 12. A distal marker 54 is located on tubular body 12 under an adhesive taper 50 adjacent the proximal end 92 of balloon 22. A distal adhesive taper 52 is provided adjacent the distal end 94 of balloon 22. Further details are provided in the above-referenced application SHAFT FOR MEDICAL CATHETERS application Ser. No. 09/026,105, filed Feb. 19, 1998, now U.S. Pat. No. 6,288,072.

In order to attach the core wire 26 to the tubular body 12, the coil 32 is first attached to the core wire 26 in a subassembly. The core wire 26 is processed as described above and cut to the desired length. In the embodiment shown in FIGS. 2 and 6, the length of the core wire is about 37 mm. The coil 32 is then cut to a desired length which is shorter than the length of the core wire. As shown in FIGS. 2 and 6, the coil length is about 35 mm. The coil 32 is then slid over the core wire into a position leaving a proximal end 48 of the core wire exposed. In the embodiment shown in FIGS. 2 and 6, the proximal end 48 of the core wire 26 is exposed about 2 mm. The coil 32 is then soldered to the core wire 26, preferably at two positions on the core wire 26. FIG. 2 shows a proximal solder 88 at an intermediate position on the core wire, and a distal solder which forms the ball 34 at distal end 30. Other locations for soldering the coil 32 to the core wire 26 are also contemplated by the invention.

This core wire-coil subassembly is then ready for insertion into tubular body 12. Proximal end 48 of core wire 26 is inserted into a lumen 18 of tubular body 12 until the coil 32 butts against tubular body 12, and core wire 26 is visible through notch 24. Core wire 26 is secured within lumen 18 by crimping tubular body 12 such that the interior surface of tubular body 12 defining lumen 18 contacts proximal end 48 and firmly secures it within lumen 18. Preferably, tubular body 12 is crimped at at least two points to secure proximal end 48 within lumen 18. As shown in FIG. 2, two crimps 38 and 40 secure the tubular body 12 to the core wire 26. In those embodiments where tubular body 12 is made of nitinol, sufficient crimping pressure must be exerted upon tubular body 12 to overcome the elastic response of nitinol. Generally, this requires exertion of sufficient pressure to deform the nitinol tubular body 12 by about 9% or more. For a nitinol tubular body 12 having an outer diameter of 0.014 inches, and an inner diameter of about 0.0095 inches, to be crimped over a nitinol core wire end 48 having an outer diameter of about 0.009 inches, it has been found that a pressure of about 120 ksi is sufficient. Other pressures may also be used provided that they are sufficient to cause tubular body 12 to securely contact core wire 26, but not so great as to unduly deform tubular body 12.

End 48 may be further sealed by use of adhesives 90 which are used to seal the balloon 22 to tubular body 12. As shown in FIG. 2, balloon 22 is sealed at a proximal end 92 to the tubular body 12, and at a distal end 94 to the coil 32 and tubular body 12. The balloon 22 is bonded to tubular body 12 and the coil 32 by the adhesive 90, preferably a cyanoacrylate such as LOCTITE 4011, although other types of adhesives may be used. The adhesive 90 is applied to the proximal and distal ends 92 and 94 of the balloon 22 and wicks into the balloon 22 up to the position of the adhesive stops 56 and 58. Further details of balloon bonding are given in the above referenced application BALLOON CATHETER AND METHOD OF MANUFACTURE, application Ser. No. 09/026,225, filed Feb. 19, 1998. This adhesive 90 acts not only to seal the balloon to the catheter, but also to aid in sealing the coil 32 to the distal end 36 of tubular body 12.

It will be appreciated that certain variations in the method of manufacture of the core wire of the present invention may suggest themselves to those skilled in the art. The foregoing detailed description is to be clearly understood as given by way of illustration, the spirit and scope of this invention being limited solely by the appended claims.

What is claimed is:

1. A medical guidewire, comprising:
    an elongate tubular body having proximal and distal sections and proximal and distal ends;
    an expandable member on the distal section of the tubular body;
    a lumen in the tubular body, the lumen extending between the proximal end of the tubular body to the distal end of the tubular body; and
    a core wire having proximal and distal sections, the core wire securely mounted on the distal end of the tubular body and constructed of a nickel titanium alloy formed by imparting superelasticity to the elongate body followed by removing superelasticity from the distal section of the elongate body to produce a shapeable tip.

2. The guidewire of claim 1, further comprising a coil around the core wire which extends from a distal end of the core wire to the distal end of the tubular body.

3. The guidewire of claim 2, wherein the coil is secured to the core wire with solder.

4. The guidewire of claim 2, wherein the coil is made of a radiopaque material.

5. The core wire of claim 1, wherein the shapeable tip is formed by heat treating the distal section of the elongate body.

6. A medical device comprising:
    a catheter; and
    a cold-worked shapeable tip on a distal section of said catheter, said tip exhibiting substantially linear elasticity, wherein the catheter has a section proximal to the distal section which exhibits transformational superelasticity.

7. The medical device of claim 6, wherein the shapeable tip is made of a nickel-titanium alloy.

8. The medical device of claim 6, wherein the shapeable tip is in a martensite phase.

9. The medical device of claim 6, wherein the catheter has a section proximal to the distal section which is substantially flexible.

10. A core wire for use in a medical device comprising:
    an elongate body having proximal and distal sections, the proximal section having superelastic properties and the distal section having a cold-worked tip from which superelasticity has been removed so that the tip is shapeable.

11. The core wire of claim 10, wherein the proximal section is made superelastic by first cold working the body followed by heat treatment.

12. The core wire of claim 10, wherein the proximal section is made superelastic by solution treatment of the body followed by aging.

13. The core wire of claim 10, wherein the shapeable tip has a flattened configuration.

14. A tip for a medical device, comprising:
    a core wire having a substantially flexible proximal section and a shapeable cold-worked distal section; and
    a coil surrounding the core wire.

15. The tip of claim 14, wherein the proximal section of the core wire exhibits transformational superelasticity and the distal section of the core wire exhibits substantially linearly elasticity.

16. The tip of claim 14, wherein the core wire has a proximal end which is attached to a distal end of the medical device.

17. A core wire having proximal and distal sections comprising:
    means for flexibility in the proximal section; and
    means for shapeability in the distal section, said shapeability means including a cold-worked tip.

* * * * *